(12) United States Patent
Pasternak et al.

(10) Patent No.: US 7,820,688 B2
(45) Date of Patent: *Oct. 26, 2010

(54) TOPICAL ANESTHETIC/OPIOID FORMULATIONS AND USES THEREOF

(75) Inventors: Gavril Pasternak, New York, NY (US); Yuri Kolesnikov, Tenafly, NJ (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/823,365

(22) Filed: Apr. 13, 2004

(65) Prior Publication Data

US 2004/0204366 A1    Oct. 14, 2004

Related U.S. Application Data

(62) Division of application No. 09/975,812, filed on Oct. 11, 2001, now Pat. No. 6,790,855.

(51) Int. Cl.
*A01N 43/42* (2006.01)
*A01N 33/02* (2006.01)
*A61K 31/44* (2006.01)
*A61K 31/135* (2006.01)
*A61K 31/16* (2006.01)

(52) U.S. Cl. ............... 514/282; 514/647; 514/626; 514/289; 514/817

(58) Field of Classification Search ............ 514/282, 514/535–537, 647, 626, 289, 817
See application file for complete search history.

(56) References Cited

U.S. PATENT DOCUMENTS

| | | | |
|---|---|---|---|
| 4,446,140 A | | 5/1984 | Nelson |
| 4,626,539 A | | 12/1986 | Aungst et al. |
| 5,028,595 A | * | 7/1991 | Soo .................. 514/49 |
| 5,321,012 A | | 6/1994 | Mayer et al. |
| 5,523,323 A | | 6/1996 | Maccecchini |
| 5,589,480 A | * | 12/1996 | Elkhoury et al. ........... 514/282 |
| 5,635,204 A | | 6/1997 | Gevirtz et al. |
| 5,654,281 A | | 8/1997 | Mayer et al. |
| 5,686,112 A | | 11/1997 | Liedtke |
| 5,689,489 A | | 11/1997 | Shin |
| 5,814,659 A | * | 9/1998 | Elden .................. 514/452 |
| 5,834,480 A | | 11/1998 | Elkhoury |
| 5,834,513 A | * | 11/1998 | Ptchelintsev et al. ........ 514/561 |
| 5,840,731 A | * | 11/1998 | Mayer et al. ............... 514/289 |
| 5,866,143 A | | 2/1999 | Elkhoury |
| 5,869,498 A | | 2/1999 | Mayer et al. |
| 5,948,389 A | | 9/1999 | Stein |
| 6,191,126 B1 | | 2/2001 | Gamache |
| 6,383,511 B1 | | 5/2002 | Cassel |

FOREIGN PATENT DOCUMENTS

| | | |
|---|---|---|
| JP | 2000-169378 | 6/2000 |
| WO | WO 94/14427 | 7/1994 |
| WO | WO 97/10815 | 3/1997 |
| WO | WO 98/14427 | 4/1998 |
| WO | WO-98/25614 | 6/1998 |
| WO | WO 98/26770 | 6/1998 |
| WO | WO 98/131358 | 7/1998 |
| WO | WO 00/03716 | 1/2000 |

OTHER PUBLICATIONS

Yoji et al. (Interaction of Intrathecally Infused Morphine and Lidocaine in Rats (Part I): Synergistic Antinociceptive Effects, Anesthesiology, Dec. 1998, vol. 89(6), pp. 1455-1463).*
Goodman and Gilman (The Pharmacological Basis of Therapeutics, seventh edition, pp. 302-305 and pp. 310-312).*
Adams et al. (1993) J. Pharmacol. Exp. Ther. 266(3): 1261-1267.
Atanassoff et al (1997) Anesth. Analg. 84: 1340-1343.
Butterworth and Strichartz (1990) Anesthesiol. 72: 711-734.

(Continued)

*Primary Examiner*—Sreeni Padmanabhan
*Assistant Examiner*—Kara R McMillian
(74) *Attorney, Agent, or Firm*—Edwards Angell Palmer & Dodge LLP; Peter C. Lauro; Mark D. Russett

(57) ABSTRACT

Many chemical and pharmaceutical compositions are known to produce antinociceptive effects that are helpful in relieving pain and inflammation. Both opioids and local anesthetics serve an important function in providing peripheral pain relief. Topical administration of pain-relieving drugs to the periphery offers important advantages over systemic or local, non-topical administration. The present invention provides topical pharmaceutical compositions, formulated with at least one local anesthetic and at least one opioid analgesic in a topical excipient. The present invention also provides methods for relieving pain in a subject through topical administration of the pharmaceutical composition in an amount and a duration sufficient to synergistically potentiate an antinociceptive response. Synergistic potentiation of analgesia through topical administration of a local anesthetic/opioid pharmaceutical composition provides a new and improved approach to peripheral pain management.

14 Claims, 7 Drawing Sheets

OTHER PUBLICATIONS

Bliss & Collingridge (1993) Nature 361: 31-39.
Catterall (1992) Science 242: 50-61.
Catterall and Mackie (1996) Goodman & Gilman's, The pharmacologic basis of therapeutics, Ninth Edition (Hardman et al eds.) McGraw-Hill pp. 331-347.
Courtney and Strichartz (1987) Handbook of Experimental Pharmacology, vol. 81. (Strichartz ed.) Springer-Verlag pp. 53-94.
Chen et al (1993) Mol. Pharmacol. 44: 8-12.
Hanson (1995) Remington: The Science and Practice of Pharmacy, 17th edition, Mack Publishing Company p. 1146-1153.
Elliot et al. (1994) Pain 56: 69-75.
He and Lee (1998) J. Pharmacol. Exp. Ther. 285: 1181-1186.
Horan et al. (1992) Life Sci. 50: 1535-1541.
Kolesnikov and Pasternak (1999) J. Pharmacol. Exp. Ther. 290(1): 247-252.
Kolesnikov et al. (1996) Eur. J. Pharmacol. 310: 141-143.
Kolenikov et al. (1996) J. Pharmacol. Exp.Ther. 279(2): 502-506.
Kolesnikov et al. (1994) Life Sci. 55: 1393-1398.
Kolesnikov et al. (1993) Proc. Natl. Acad.Sci. USA 90: 5162-5166.
Kolesnikov Y.A. et al. "Peripheral blockade of topical morphine tolerance by ketamine" European Journal of Pharmacology, 1999, 374/2.
Lutz and Pfister (1992) J. Receptor Res. 12: 267-286.
Olson et al. (1989) Peptides 10: 1253-1280.
Pasternak (1993) Clin. Neuropharmacol. 16(1): 1-18.
Portoghese et al. (1992) Eur. J. Pharmacol. 218: 195-196.
Reisine and Pasternak (1996) Goodman & Gilman's, The pharmacological basis of Therapeutics, Ninth Edition (Hardman et al. Eds.) McGraw-Hill pp. 521-555.
Rossi et al (1994) Brain Res. 665: 85-93.
Saito et al. (1998) Anesthesiol. 89: 1455-1463.
Saito et al (1998) Anesthesiol 89: 1464-1470.
Sibinga et al. (1998) Annu. Rev. Immunol. 6: 219-249.
Simon (1991) Medicinal res. Rev. 11: 357-374.
Sofuoglu et al. (1991) J. Pharmacol. Ther. 257(2): 676-680.
Standifer and Pasternak (1997) Cell Signal. 9, (No. 3/4): 237-248.
Standifer et al. (1996) Mol. Pharmacol. 50: 293-298.
Trujillo and Akil (1991) Science 251: 85-86.
Yasuda et al (1993) Proc. Natl. Acad.Sci. USA 90: 6736-6740.
Yeung and Rudy (1980) J. Pharmacol. Exp. Ther. 215(3): 633-642.
Kolesnikov Yuri A et al. "Analgesic synergy between topical lidocaine and topical opioids" Journal of Pharmacology and Experimental Therapeutics, vo. 295, No. 2, Nov. 2000 pp. 546-551, XP 001080389.
Khoury G F et al. "Intraarticular Morphine, Bupivacaine, and Morphine/Bupivacaine for pain control after knee videoarthroscopy" Anesthesiology, American Society of Anesthesiologists, Philadelphia, PA, US, vol. 77, No. 263, 1992, pp. 263-266, XP000910063.
Kaneko Megumi et al. "Synergistic antinociceptice interaction after epidural coadministration of morphine and lidocaine in rats." Anesthesiology, vol. 80, No. 1, 1994, pp. 137-150, XP001080405.
Saito Yoji et al. "Interaction of intrathecally infused morphine and lidocaine in rats (Part 1)." Anesthesiology (Hagerstown), vol. 89, No. 6, Dec. 1998 pp. 1455-1463, XP001080402.
Atanassoff Peter G et al. "The effect of intradermal administration of lidocaine and morphine on the response to thermal stimulation." Anesthesia & Analgesia, vol. 84, No. 6, 1997, pp. 1340-1343, XP001079098.
Roy et al. "Transdermal Delivery of Narcotic Analgesics: Comparative Metabolism and Permeability of Human Cadaver Skin and Hairless Mouse Skin" Journal of Pharmaceutical Sciences, vol. 83 (12) Dec. 1994, pp. 1723-1728.
Roy et al. "Transdermal Delivery of Narcotic Analgesics:Comparative Permeabilities of Narcotic Analgesics Through Human Cadaver Skin", Pharmaceutical Research, vol. 6(10) 1989, pp. 825-832.
Picard et al, "Analgesic efficacy of peripheral opioids (all except intra-articular): a qualitative systematic review of randomized controlled trials" Pain , Sep. 72(3) 1997, 309-318.
Moore et al. "The efficacy of locally applied morphine in postoperative pain afterbilateral third molar surgery." Br J Clin Pharmacol Mar. 1994 37(3):227-30.
Leopold et al. "Percutaneous Penetration of Local Anasthetic Bases: Pharmacodynamic Measurements" The Journal of Investigative Dermatology, vol. 113(3), Sep. 1999, pp. 304-307.
Saito et al. Interaction of Intrathecally Infused Morphine and Lidocaine in Rats (Part 1), Anesthesiology, vol. 89, 1988, pp. 1455-1463.
Raja et al. "Comparison of postoperative analgesic effects of intraarticular bupivacaine and morphine following arthroscopic knee surgery." Anesthesiology Dec. 1992, 77(6): pp. 1143-1147.
Rosseland et al. "Intra-articular morphine for pain relief after knee arthroscopy" Acta Anaesthesiol Scand Mar. 1999 43(3): 252-7.
Fletcher et al. "Additivity of bupivacaine and morphine for peripheral analgesia in rats." Fundam Clin Pharmacol. Jul.-Aug. 2000: 14(4), pp. 327-334.
Yarussi et al. "Evaluation of peripheral morphine analgesia for lumpectomy and axillary node dissection: a randomized, double-blind, placebo-controlled study." Reg. Anesth Pain Med, Mar.-Apr. 1999: 24(2), pp. 142-145.
Rosenstock et al. "Analgesic effect of incisional morphine following inguinal herniotomy under spinal anesthesia" Reg Anesth Mar.-Apr. 1996 21(2), pp. 93-98.
Merriam-Webster's Collegiate Dictionary. 10ed. (1999), "potentiate" p. 912, Merriam-Webster, Incorporated.
Kolesnikov, Yuri A., et al., Analgesic Synergy Between Topical Morphine and Butamben in Mice, Department of Anesthesiology and Laboratory of Molecular Neuropharmacology, Memorial-Sloan Kettering Cancer Center, New York, NY , Anesth Analg 2003;97-1103-7.
Kaneko et al. "Interaction of intrathecally infused morphine and lidocaine in rats (part I): synergistic anticociptive effects." Anesthesiology 89(6), (1998) Abstract only.
Muller et al. "Cancer pain: beneficial effect of ketamine addition to spinal administration of morphine-clonidine-lidocaine mixture." Ann Fr. Anesth Reanim 15(3), (1996) Abstract only.
Katzung Basic and Clinical Pharmacology, p. 402 (1995) Abstract only.
Moore et al. "Topical Morphine in a Canine Model: A Pilot Study." PUB MED Abstract PMID 9749679 (1998).
Krajnik et al. "Potential Uses of Topical Poioids in Palliative Care-Report of 6 cases." PMID 10204724 (1999).
Twillman et al. "Treatment of Painful Skin Ulcers with Topical Opioids." PMID 10203881 (1999).
The European Examination Report dated Dec. 11, 2008, from corresponding EPO application No. 01 930 827.9.

* cited by examiner a.

b.

a.

b.

a.

* $p < 0.05$ b.

a.

b.

TOPICAL ANESTHETIC/OPIOID FORMULATIONS AND USES THEREOF

CROSS-REFERENCE TO RELATED APPLICATIONS

This application is a division of U.S. patent application Ser. No. 09/975,812, filed on Oct. 11, 2001 now U.S. Pat. No. 6,790,855. This application further claims the benefit of and priority to U.S. Patent Application Ser. Nos. 60/200,437, filed Apr. 28, 2000 and 09/844,111 filed Apr. 27, 2001. Each of these applications and each document cited or referenced in each of these applications, including during any prosecution ("application cited documents"), and each document cited or referenced in each of the application cited documents, are hereby incorporated herein by reference.

STATEMENT OF RIGHTS TO INVENTIONS MADE UNDER FEDERALLY SPONSORED RESEARCH

This work was supported by the government, in part, by grants from the National Institute of Drug Abuse, No. DA07241. The government has certain rights to this invention.

TECHNICAL FIELD

The present invention relates to a topical pharmaceutical composition, formulated with at least one local anesthetic and at least one opioid analgesic, and to methods of providing pain relief to a subject through topical administration of the composition in an amount and a duration sufficient to synergistically potentiate an antinociceptive response.

BACKGROUND ART

Many chemical and pharmaceutical compositions are known to produce antinociceptive effects. These include, for instance, steroids; non-steroidal anti-inflammatory drugs; local anesthetics; and opioids. These antinociceptive drug classes are useful for modulating many different types of pain, including postoperative, acute, chronic and inflammatory pain. Pain can be alleviated systemically for instance by ingestion or parenteral administration of a suitable composition or, at the site of the pain for instance, by local or topical administration thereof.

Opiates are drugs derived from opium and include morphine, codeine and a wide variety of semisynthetic opioid congeners derived from these and from the baine, another component of opium. Opioids include the opiates and all agonists and antagonists with morphine-like activity and naturally occurring endogenous and synthetic opioid peptides. Although morphine and other morphine-like opioid agonists are commonly used to produce analgesia, the severity and high incidence of side effects limits their use.

There are now many compounds with pharmacological properties similar to those produced by morphine, but none has proven to be clinically superior in relieving pain. References to morphine herein will be understood to include morphine-like agonists as well. The effects of morphine on human beings are relatively diverse and include analgesia, drowsiness, mood changes, respiratory depression, decreased gastrointestinal motility, nausea, vomiting, and alterations of the endocrine and autonomic nervous systems. Pasternak (1993) Clin. Neuropharmacol. 16:1. Doses of morphine need to be tailored based on individual sensitivity to the drug and the pain-sparing needs of the individual. For instance, the typical initial dose of morphine (10 mg/70 kg) relieves postoperative pain satisfactorily in only two-thirds of patients. Likewise, responses of an individual patient can vary dramatically with different morphine-like drugs and patients can have side effects with one such drug and not another. For example, it is known that some patients who are unable to tolerate morphine may have no problems with an equianalgesic dose of methadone. The mechanisms underlying individual variations in response to morphine and morphine-like agonists have not been defined.

The analgesic effects of morphine are transduced through opioid receptors in the central nervous system (CNS), located at both spinal and multiple supraspinal sites. Morphine and its agonists induce profound analgesia when administered intrathecally or instilled locally into the dorsal horn of the spinal cord. Recently, it has been shown that opioids elicit analgesia at peripheral sites and therefore, topical administration of morphine is also effective in modulating pain. Several mechanisms of action are believed to mediate the inhibition of nociceptive reflexes from reaching higher centers of the brain, including the inhibition of neurotransmitter release by opioid receptors on the termini of primary afferent nerves and post-synaptic inhibitory actions on interneurons and on the out-put neurons of the spinothalamic tract.

The instillation of morphine into the third ventricle or within various sites in the midbrain and medulla, most notably the periaqueductal gray matter, the nucleus raphe magnus, and the locus ceruleus results in profound analgesia. Although the neuronal circuitry responsible has not been defined, this produces enhanced activity in the descending aminergic bulbospinal pathways that exert inhibitory effects on the processing of nociceptive information in the spinal cord. Simultaneous administration of morphine at both spinal and supraspinal sites results in a synergized analgesic response, with a ten-fold reduction in the total dose of morphine necessary to produce equivalent analgesia at either site alone.

Morphine also exerts effects on the neuroendocrine system. Morphine acts in the hypothalamus to inhibit the release of gonadotropin releasing hormone (GnRH) and corticotropin-releasing factor (CRF), thus decreasing circulating concentrations of luteinizing hormone (LH), follicle stimulating hormone (FSH), adrenocorticotropin (ACTH), and β-endorphin. As a result of the decreased concentrations of pituitary trophic hormones, the plasma concentrations of testosterone and cortisol decline. The administration of opiates increases the concentration of prolactin (PRL) in plasma, most likely by reducing the dopaminergic inhibition of PRL secretion. With chronic administration, tolerance eventually develops to the effects of morphine on hypothalamic releasing factors.

Opiates can interfere with normal gastrointestinal functioning. Morphine decreases both gastric motility and stomach secretion of hydrochloric acid. Morphine can delay passage of gastric contents through the duodenum for as long as 12 hours. Morphine also decreases biliary, pancreatic, and intestinal secretions and delays the digestion of food in the small intestine. Propulsive peristaltic waves in the colon are diminished or abolished after administration of morphine and commonly, constipation occurs. For a detailed review of the physiologic effects of morphine, see Reisine and Pasternak (1996) Goodman & Gilnan's, The pharmacological basis of therapeutics, Ninth Edition (Hardman et al. eds.) McGraw-Hill pp. 521-555.

Morphine also exerts effects on the immune system. The most firmly established immunologic effect of morphine is its ability to inhibit the formation of human lymphocyte rosettes.

The administration of morphine to animals causes suppression of the cytotoxic activity of natural killer cells and enhances the growth of implanted tumors. These effects appear to be mediated by actions within the CNS. By contrast, β-endorphin enhances the cytotoxic activity of human monocytes in vitro and increases the recruitment of precursor cells into the killer cell population; this peptide also can exert a potent chemotactic effect on these cells. A novel type of receptor (designated ε) may be involved. These effects, combined with the synthesis of proopiomelanocortin (POMC) and preproenkephalin by various cells of the immune system, have stimulated studies of the potential role of opioids in immune function regulation. Sibinga et al. (1988) Annu. Rev. Immunol. 6:219.

Side effects resulting from the use of morphine range from mild to life-threatening. Morphine causes constriction of the pupil by an excitatory action on the parasympathetic nerve innervating the pupil. Morphine depresses the cough reflex through inhibitory effects on the cough centers in the medulla. Nausea and vomiting occur in some individuals through direct stimulation of the chemoreceptor trigger zone for emesis, in the postrema of the medulla. Therapeutic doses of morphine also result in peripheral vasodilatation, reduced peripheral resistance and inhibition of baroreceptor reflexes in the cardiovascular system.

Additionally, morphine provokes the release of histamines, which can cause hypotension. Morphine depresses respiration, at least in part by direct effects on brainstem regulatory systems. In humans, death from morphine poisoning is nearly always due to respiratory arrest. Opioid antagonists can produce a dramatic reversal of severe respiratory depression; naloxone is currently the treatment of choice. High doses of morphine and related opioids can produce convulsions that are not always relieved by naloxone.

The development of tolerance and physical dependence with repeated use is a characteristic feature of all opiates. Dependence seems to be closely related to tolerance, since treatments that block tolerance to morphine also block dependence. In vivo studies in animal models demonstrate the importance of neurotransmitters and their interactions with opioid pathways in the development of tolerance to morphine. Blockade of glutamate actions by noncompetitive and competitive NMDA (N-methyl-D-aspartate) antagonists blocks morphine tolerance. Trujillo and Akil (1991) Science 251:85; Elliott et al. (1994) Pain 56:69; U.S. Pat. Nos. 5,654,281; 5,523,323; and 5,321,012; and WO/98/14427. NMDA antagonists include, but are not limited to, dextromethorphan, dextrorphan, ketamine, pyroloquinoline quinone, cis-4-(phosphonomethyl)-2-piperdine carboxylic acid, and MK801. Blockade of the glycine regulatory site on NMDA receptors exerts similar effects to block tolerance. Kolesnikov et al. (1994) Life Sci. 55:1393. Administering inhibitors of nitric oxide synthase in morphine-tolerant animals reverses tolerance, despite continued opioid administration. Kolesnikov et al. (1993) Proc. Natl. Acad. Sci. USA 90:5162.

These studies illustrate several important aspects of tolerance and dependence. First, the selective actions of drugs on tolerance and dependence demonstrate that analgesia can be dissociated from these two unwanted actions. Second, the reversal of preexisting tolerance by NMDA antagonists and nitric oxide synthase inhibitors indicates that tolerance is a balance between activation of processes and reversal of those processes. These observations suggest that, by use of selective agonists and/or antagonists, tolerance and dependence in the clinical management of pain can be minimized or disassociated from the therapeutic effects. Unfortunately, NMDA antagonists are difficult to administer systemically due to their profound psychomimetic and dysphoric actions.

In addition to morphine, a variety of opioids are suitable for clinical use. These include, but are not limited to, Levorphanol, Meperidine, Fentanyl, Methadone, Codeine, Propoxyphene and various opioid peptides. Certain opioids are mixed agonists/antagonists and partial agonists. These include pentazocine, nalbuphine, butorphanol, and buprenorphine.

The pharmacological effects of levorphanol closely parallel those of morphine although clinical reports suggest that levorphanol produces less nausea. Dextromethorphan, the d-isomer of the codine analog of levorphanol, has been used specifically for the treatment of mouth pain. See, U.S. Pat. No. 4,446,140.

Meperidine exerts its chief pharmacological effects on the CNS and the neural elements in the bowel. Meperidine produces a pattern of effects similar, but not identical to, those described for morphine. In equianalgesic doses, meperidine produces as much sedation, respiratory depression, and euphoria as morphine. The pattern of unwanted side effects that follows the use of meperidine are similar to those observed after equianalgesic doses of morphine, except that constipation and urinary retention are less common.

Fentanyl is a synthetic opioid estimated to be 80 times as potent as morphine as an analgesic. High doses of fentanyl can result in severe toxicity and produce side effects including muscular rigidity and respiratory depression.

Methadone is an opioid with pharmacologic properties similar to morphine. The pharmacologic properties of methadone include effective analgesic activity, efficacy by the oral route and persistent effects with repeated administration. Side effects include detection of miotic and respiratory-depressant effects for more than 24 hours after a single dose, and, marked sedation is seen in some patients. Effects on cough, bowel motility, biliary tone and the secretion of pituitary hormones are qualitatively similar to those of morphine. In contrast to morphine, codeine is approximately 60% as effective orally as parenterally, both as an analgesic and as a respiratory depressant.

Codeine has an exceptionally low affinity for opioid receptors, the analgesic effect of codeine is due to its conversion to morphine. However, codeine's antitussive actions probably involve distinct receptors that specifically bind codeine.

Propoxyphene produces analgesia and other CNS effects that are similar to morphine. It is likely that at equianalgesic doses the incidence of side effects such as nausea, anorexia, constipation, abdominal pain, and drowsiness would be similar to those of codeine.

Opioid antagonists have therapeutic utility in the treatment of overdosage with opioids. As understanding of the role of endogenous opioid systems in pathophysiologic states increases, additional therapeutic indications for these antagonists will emerge. If endogenous opioid systems have not been activated, the pharmacologic actions of opioid antagonists depend on whether or not an opioid agonist has been administered previously, the pharmacologic profile of that opioid and the degree to which physical dependence on an opioid has developed. The antagonist naloxone produces no discernible subjective effects aside from slight drowsiness. Naltrexone functions similarly, but with higher oral efficacy and a longer duration of action. Currently, naloxone and naltrexone are used clinically to treat opioid overdoses. Their potential utility in the treatment of shock, stroke, spinal cord and brain trauma, and other disorders that can involve mobilization of endogenous opioids remains to be established.

The complex interactions of morphine and drugs with mixed agonist/antagonist properties are mediated by multiple classes of opioid receptors. Opioid receptors comprise a family of cell surface proteins, which control a range of biological responses, including pain perception, modulation of affective behavior and motor control, autonomic nervous system regulation and neuroendocrinologic function. There are three major classes of opioid receptors in the CNS, designated mu, kappa and delta, which differ in their affinity for various opioid ligands and in their cellular distribution. The different classes of opioid receptors are believed to serve different physiologic functions. Olson et al. (1989) Peptides 10:1253; Lutz and Pfister (1992) J. Receptor Res. 12:267; and Simon (1991) Medicinal Res. Rev. 11:357. Morphine produces analgesia primarily through the mu-opioid receptor. However, among the opioid receptors, there is substantial overlap of function as well as of cellular distribution.

The mu-opioid receptor mediates the actions of morphine and morphine-like opioids, including most clinical analgesics. In addition to morphine, several highly selective agonists have been developed for mu-opioid receptors, including [D-Ala$^2$,MePhe$^4$,Gly(ol)$^5$]enkephalin (DAMGO), levorphanol, etorphine, fentanyl, sufentanil, bremazocine and methadone. Mu-opioid receptor antagonists include naloxone, naltrexone, D-Phe-Cys-Try-D-Trp-Orn-Thr-Pen-Thr-NH$_2$ (CTOP), diprenorphine, β-finaltrexamine, naloxonazine, nalorphine, nalbuphine, and naloxone benzoylhydrazone. Differential sensitivity to antagonists, such as naloxonazine, indicates the pharmacologic distinctions between the mu-opioid receptor subtypes, mu$_1$ and mu$_2$. Several of the opioid peptides also interact with mu-opioid receptors.

There are three known kappa-opioid receptor subtypes, designated kappa$_1$, kappa$_2$ and kappa$_3$. Each kappa-opioid receptor subtype possesses distinct pharmacologic properties. For example, kappa$_1$-opioid receptors produce analgesia spinally and kappa$_3$-opioid receptors relieve pain through supraspinal mechanisms. In addition, the kappa$_1$-opioid receptor selectively binds to the agonist U50,488. Additional agonists of the kappa$_1$-opioid receptor include etorphine; sufentanil; butorphanol; β-finaltrexamine; nalphorine; pentazocine; nalbuphine; bremazocine; ethylketocyclazocine; U50,488; U69,593; spiradoline; and nor-binaltorphimine. Agonists of the kappa$_3$-opioid receptor include etorphine; levorphanol; DAMGO; nalphorine; nalbuphine; naloxone benzoylhydrazone; bremazocine; and ethylketocyclazocine. Effects of agonists on the kappa$_1$-opioid receptors are reversed by a number of antagonists, including buprenorphine, naloxone, naltrexone, diprenorphine, naloxonazine, naloxone benzoylhydrazone, naltrindole and nor-binaltorphimine. Antagonists of the kappa$_3$-opioid receptors include naloxone, naltrexone and diprenorphine.

The delta-opioid receptors are divided into two subclasses, delta$_1$ and delta$_2$. The delta opioid receptors modulate analgesia through both spinal and supraspinal pathways. The two subclasses were proposed based on their differential sensitivity to blockade by several novel antagonists. Portoghese et al. (1992) Eur. J. Pharmacol. 218:195; and Sofuoglu et al. (1991) J. Pharmacol. Ther. 257:676. The agonists [D-Pro$^2$,Glu$^4$]deltorphin and [D-Ser$^2$,Leu$^5$]enkephalin-Thr$^6$ (DSLET) preferentially bind to the delta$_2$ receptors, whereas [D-Pen$^2$,D-Pen$^5$]enkephalin (DPDPE) has a higher affinity for delta$_1$ receptors.

There are three distinct families of endogenous opioid peptides, the enkephalins, endorphins and dynorphins. Each such peptide is derived from a distinct precursor polypeptide. Mu-opioid receptors have a high affinity for the enkephalins as well as β-endorphin and dynorphin A. The enkephalins are also endogenous ligands for the delta receptors, along with dynorphin A and dynorphin B. The kappa$_1$-opioid receptor endogenous opioid peptide agonists include dynorphin A, dynorphin B and α-neoendorphin. See Reisine and Pasternak (1996).

Members of each known class of opioid receptor have been cloned from human cDNA and their predicted amino acid sequences have been determined. Yasuda et al. (1993) Proc. Natl. Acad. Sci. USA 90:6736; and Chen et al. (1993) Mol. Phannacol. 44:8. The opioid receptors belong to a class of transmembrane spanning receptors known as G-protein coupled receptors. G-proteins consist of three tightly associated subunits, α, β and γ (1:1:1) in order of decreasing mass. Signal amplification results from the ability of a single receptor to activate many G-protein molecules, and from the stimulation by G-α-GTP of many catalytic cycles of the effector. Most opioid receptor-mediated functions appear to be mediated through G-protein interactions. Standifer and Pasternak (1997) Cell Signal. 9:237. Antisense oligodeoxynucleotides directed against various G-protein α subunits were shown to differentially block the analgesic actions of the mu-, delta-, and kappa-opioid agonists in mice. Standifer et al. (1996) Mol. Pharmacol. 50:293.

Local anesthetics prevent or relieve pain by interrupting nerve conduction. When applied locally to nerve tissue in appropriate concentrations, local anesthetics reversibly block the action potentials responsible for nerve conduction. In general, their action is restricted to the site of application and rapidly reverses upon diffusion from the site of action in the nerve. The necessary practical advantage of the local anesthetics is that their action is reversible at clinically relevant concentrations; their use is followed by complete recovery in nerve function with no evidence of damage to nerve fibers or cells. For a detailed review of local anesthetics, see Catterall and Mackie (1996) Goodman & Gilman's, The pharmacologic basis of therapeutics, Ninth Edition (Hardman et al. eds.) McGraw-Hill pp. 331-347; and Hanson (1995) Remington: The Science and Practice of Pharmacy, 17th edition, Mack Publishing Company pp. 1146-1153.

Local anesthetics can be administered by a variety of routes, including topical, infiltration, field or nerve block, intravenous regional, spinal, or epidural, as dictated by clinical circumstances. Local anesthetics act on any part of the nervous system and on every type of nerve fiber. Thus, a local anesthetic in contact with a nerve trunk can cause both sensory and motor paralysis in the area innervated. A wide variety of topical anesthetics are available. These include, but are not limited to, Benzocaine, cocaine, cocaine hydrochloride, Dibucaine, Dyclonine Hydrochloride, Lidocaine, Pramoxine Hydrochloride, Proparacaine Hydrochloride, Tetracaine, benoxinate, hydrochloride, butamben picrate, butamben oil, clove oil, eugenol and combinations thereof such as Benzocaine, Butamben and Tetracaine Hydrochloride; and Benzalkonium chloride and Lidocaine Hydrochloride. See, e.g., Remington (1995) for descriptions of the compositions and uses thereof. The salts and base forms of the esters and amides of these anesthetics produce topical anesthesia. The salts do not penetrate intact skin, but both forms penetrate abraded or raw granulated skin surfaces. The base forms relieve pruritus, burning and surface pain on intact skin, but penetrate only to a limited degree. Wounds, ulcers and burns are preferably treated with preparations relatively insoluble in tissue fluids.

Mucous membranes of the nose, mouth, pharynx, larynx, trachea, bronchi and urethra are anesthetized readily by both salt and base forms. Consequently, these agents are used prior to inserting intratracheal catheters, pharyngeal and nasal airways, nasogastric and endoscopic tubes, urinary catheters, laryngoscopes, proctoscopes, sigmoidoscopes and vaginal specula. Many of these agents are also used in the eye for such procedures as tonometry, gonioscopy and for removal of foreign bodies from the cornea or conjunctiva. Remington (1995).

Although a variety of physicochemical models have been proposed to explain how local anesthetics achieve conduction block, it is now generally accepted that the major mechanism of action of these drugs involves their interaction with one or more specific binding sites within the $Na^+$ channel. For review, see Courtney and Strichartz (1987) Handbook of Experimental Pharmacology, Vol. 81. (Strichartz ed.) Springer-Verlag pp. 53-94. Local anesthetics prevent the generation and the conduction of nerve impulses through direct interaction with voltage-gated $Na^+$ channels located in the cell membrane. They bind to a specific receptor site within the pore of the $Na^+$ channel, blocking ion movement through this pore. This action decreases or prevents the large transient increase in the permeability of excitable membranes to $Na^+$ that is normally produced by a slight depolarization of the membrane. As anesthetic action progressively develops in the nerve, the threshold for electrical excitability gradually increases, the rate of rise of the action potential declines, impulse conduction slows, and the safety factor for conduction decreases; these factors decrease the probability of propagation of the action potential, and nerve conduction fails.

The degree of block produced by a given concentration of local anesthetic depends on how the nerve has been stimulated and on its resting membrane potential. Thus, a resting nerve is much less sensitive to a local anesthetic than is one that is repetitively stimulated; higher frequency of stimulation and more positive membrane potential cause a greater degree of anesthetic block. Local anesthetic frequency- and voltage-dependent effects occur because the local anesthetic molecule, in its charged form, gains access to its binding site within the pore only when the $Na^+$ channel is in an open state, as the local anesthetic binds more tightly to and stabilizes the inactivated state of the $Na^+$ channel. Courtney and Strichartz (1987); and Butterworth and Strichartz (1990) Anesthesiol. 72:711. Generally, local anesthetic action frequency-dependence depends critically on the dissociation rate from the receptor site in the pore of the $Na^+$ channel. A high stimulation frequency is required for rapidly dissociating drugs so that drug binding during the action potential exceeds dissociation between action potentials.

Biochemical, biophysical, and molecular biological investigations during the past decade have led to a rapid expansion of knowledge about the structure and function of the $Na^+$ channel and other voltage-gated ion channels. Catterall (1992) Science 242:50. The $Na^+$ channels of the mammalian brain are heterotrimeric complexes of glycosylated proteins with an aggregate molecular size in excess of 300 kDa; the individual subunits are designated a (260 kDa), $\beta_1$ (36 kDa), and $\beta_2$ (33 kDa). The large $\alpha$ subunit of the $Na^+$ channel contains four homologous domains (I to IV); each domain is thought to consist of six transmembrane domains or spans in $\alpha$-helical conformation. The $Na^+$-selective transmembrane pore of the channel is presumed to reside in the center of a nearly symmetrical structure formed by the four homologous domains. The voltage-dependence of channel opening is hypothesized to reflect conformational changes that result from the movement of "gating charges" (voltage sensors) in response to changes in the transmembrane potential.

The metabolic fate of local anesthetics is of great practical importance, because their toxicity depends largely on the balance between their rates of absorption and elimination. Since toxicity is related to the free concentration of drug, binding of the anesthetic to serum proteins and tissues reduces the concentration of free drug in systemic circulation and, consequently, reduces toxicity. In the case of topically applied local anesthetics, systemic absorption is so low that systemic toxicity is rarely an issue.

Lidocaine (XYLOCAINE), introduced in 1948, is now the most widely used local anesthetic. Lidocaine shares pharmacologic actions with other local anesthetic drugs. Lidocaine is an aminoethylamide and is the prototypical member of this class of local anesthetics. It is a good choice for individuals sensitive to ester-type local anesthetics.

The chemical and pharmacologic properties of each drug determine its clinical use. Lidocaine has a wide range of clinical uses as a local anesthetic; it has utility in almost any application where a local anesthetic of intermediate duration is needed. Lidocaine is also used as an antiarrhythmic agent. Lidocaine blocks both open and inactivated cardiac $Na^+$ channels. Recovery from block is very rapid, so lidocaine exerts greater effects in depolarized (e.g., ischemic) and/or rapidly driven tissues.

Some local anesthetic agents are too toxic to be given by injection. Their use is restricted to topical application to the eye, the mucous membranes, or the skin. Many local anesthetics are suitable, however, for infiltration or injection to produce nerve block; some of them also are useful for topical application. Some anesthetics are either too irritating or too ineffective to be applied to the eye. However, they are useful as topical anesthetic agents on the skin and/or mucous membranes. These preparations are effective in the symptomatic relief of anal and genital pruritus, poison ivy rashes, and numerous other acute and chronic dermatoses. They are sometimes combined with a glucocorticoid or antihistamine and are available in a number of proprietary formulations.

Dibucaine (NUPECAINAL) is a quinoline derivative. Its toxicity resulted in its removal from the U.S. market as an injectable preparation; however, it is widely popular outside the U.S. as a spinal anesthetic and is currently available as a cream and an ointment for use on the skin.

Dyclonine hydrochloride (DYCLONE) has rapid onset of action and duration of effect comparable to procaine. It is absorbed through the skin and mucous membranes. The compound is used as 0.5% or 1.0% solution for topical anesthesia during endoscopy, for oral mucositis pain following radiation or chemotherapy, and for anogenital procedures.

Pramoxine hydrochloride (ANUSOL, TRONOTHANE, others) is a surface anesthetic agent that is not a benzoate ester. Its distinct chemical structure can help minimize the danger of cross-sensitivity reactions in patients allergic to other local anesthetics. Pramoxine produces satisfactory surface anesthesia and is reasonably well tolerated on the skin and mucous membranes. It is usually too irritating to be used on the eye or in the nose. Various preparations are available for topical application, usually including 1% pramoxine.

Some local anesthetics are poorly soluble in water and, consequently, too slowly absorbed to be toxic. They can be applied directly to wounds and ulcerated surfaces, where they remain localized for long periods of time to produce a sustained anesthetic action. Chemically, they are esters of paraaminobenzoic acid which lack the terminal amino group of the previously described local anesthetics. The most important member of this series is benzocaine (ethyl aminobenzoate or AMERICAINE ANESTHETIC). Benzocaine is structurally similar to procaine, differing by the lack of a terminal diethylamino group. It is incorporated into a large number of topical preparations. Benzocaine has been reported to cause methemoglobinemia; dosing recommendations must be carefully followed.

Anesthesia of the cornea and conjuctiva can be obtained readily by topical application of local anesthetics. However, most of the local anesthetics described above can be irritating when administered for ophthalmologic use. The two compounds most frequently used are proparacaine (ALCAINE, OPHTHAINE, others) and tetracaine. Proparacaine has the advantage of bearing little antigenic similarity to the other benzoate local anesthetics and therefore, can be used in individuals sensitive to the amino ester local anesthetics.

For use in ophthalmology, suitable local anesthetics are instilled a single drop at a time. If anesthesia is incomplete, successive drops are applied until satisfactory conditions are obtained. The duration of anesthesia is determined chiefly by the vascularity of the tissue; thus anesthesia is longest in normal cornea and least in inflamed conjunctiva. In the latter, repeated instillations are necessary to maintain adequate anesthesia for the duration of the procedure. Long-term administration of topical anesthesia to the eye causes retarded healing and pitting, sloughing of the corneal epithelium and predisposition of the eye to inadvertent injury. Thus, these drugs are not usually prescribed for self-administration.

Topical administration of pain-relieving drugs to the periphery offers important advantages over systemic or local, non-topical administration. For example, topical administration of opioids decreases side effects, such as sedation, respiratory depression and nausea. Even transdermal administration of opioids can elicit systemic responses and thus, produce unwanted side effects. See U.S. Pat. Nos. 5,686,112; and 4,626,539. Benefits associated with topical administration of opioid analgesic drugs are discussed in U.S. Pat. Nos. 5,589,480; 5,866,143; and 5,834,480. Even further, limiting drug delivery to the actual site of administration can eliminate peripheral side effects such as constipation.

Topically administered morphine activity has been measured by the radiant heat tailflick assay in mice. Kolesnikov and Pasternak (1999) J. Pharmacol. Exp. Ther. 290:247. This assay, determined that analgesia provided by topical morphine is restricted to tail regions exposed to the drug. Opioids acting through kappa and delta receptors also exhibit peripheral activity. Kolesnikov and Pasternak (1999); and Kolesnikov et al. (1996) Eur. J. Pharmacol. 310:141. It has been shown that NMDA antagonists block opioid tolerance when applied topically. Kolesnikov and Pasternak (1999). Topical administration of NMDA antagonists to the periphery circumvents the undesirable side effects that preclude systemic use. Utilization of topical drug delivery allows for the combined use of opioids and NMDA antagonists.

Opioids are known to work in combination with other classes of drugs. See U.S. Pat. Nos. 5,840,731; and 5,869, 498; and WO 97/10815. Synergistic potentiation of opioid-induced analgesia is the most highly desirable effect for the clinical management of pain. This phenomenon was first observed between supraspinal and spinal sites (Yeung and Rudy (1980) J. Pharmacol. Exp. Ther. 215:633), and has since been observed between brainstem nuclei (Rossi et al. (1993) Brain Res. 665:85), as well as between peripheral and central sites (Kolesnikov et al. (1996) J. Pharmacol. Exp. Ther. 279: 247). Synergy occurs between opioids of different classes. Adams et al. (1993) J. Pharmacol. Exp. Ther. 266:1261; He and Lee (1998) J. Pharmacol. Exp. Ther. 285:1181; Horan et al. (1992)-Life Sci. 50:1535; and Rossi et al. (1994) Brain Res. 665:85. Clinical studies have shown that the systemic administration of lidocaine and opioids effectively reduces pain. Atanassoff et al. (1997) Anesth. Analg. 84:1340; Saito et al. (1998) Anesthesiol. 89:1455; and Saito et al. (1998) Anesthesiol. 89:1464. Currently, pharmacologic relationships between these two classes of drugs are not well characterized.

DISCLOSURE OF THE INVENTION

The invention encompasses pharmaceutical compositions comprising at least two compounds, at least one effecting opioid analgesia and at least one effecting local anesthesia, in amounts sufficient to potentiate an antinociceptive response when both compounds are topically administered in a physiologically acceptable topical excipient.

The invention further encompasses a method of providing topical analgesia to a subject comprising topical administration of a pharmaceutical composition comprising at least two compounds, at least one effecting opioid analgesia and at least one effecting local anesthesia, wherein the pharmaceutical composition is administered in a physiologically acceptable topical excipient and in an amount and a duration sufficient to potentiate an antinociceptive response.

BRIEF DESCRIPTION OF THE DRAWINGS

In FIG. 1b, Lidocaine (2 mM) is shown in closed circles, Lidocaine (4 mM) is shown in open circles and morphine (15 mM) is shown in closed triangles.

FIG. 3b depicts the synergistic effect of the use of morphine and lidocaine.

In FIG. 5b, buprenorphine alone is shown by an open circle; lidocaine alone is shown by a closed triangle; a combination of buprenorphine and lidocaine is shown by a closed circle; and naloxone with the buprenorphine/lidocaine combination is shown by a closed diamond.

BEST MODE FOR CARRYING OUT THE INVENTION

Figure 1:
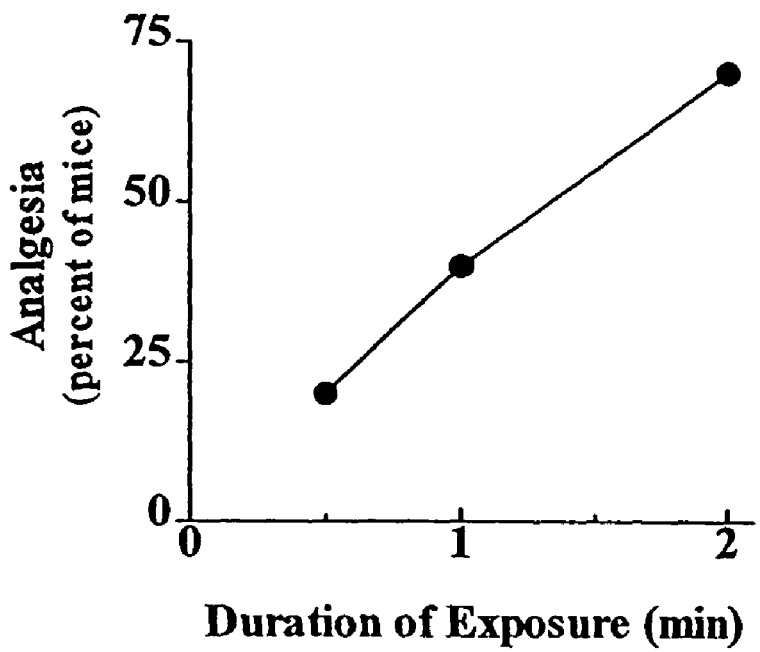
FIG. 1 is a set of graphs depicting time dependence of topical lidocaine analgesia in mice.
Figure 1:
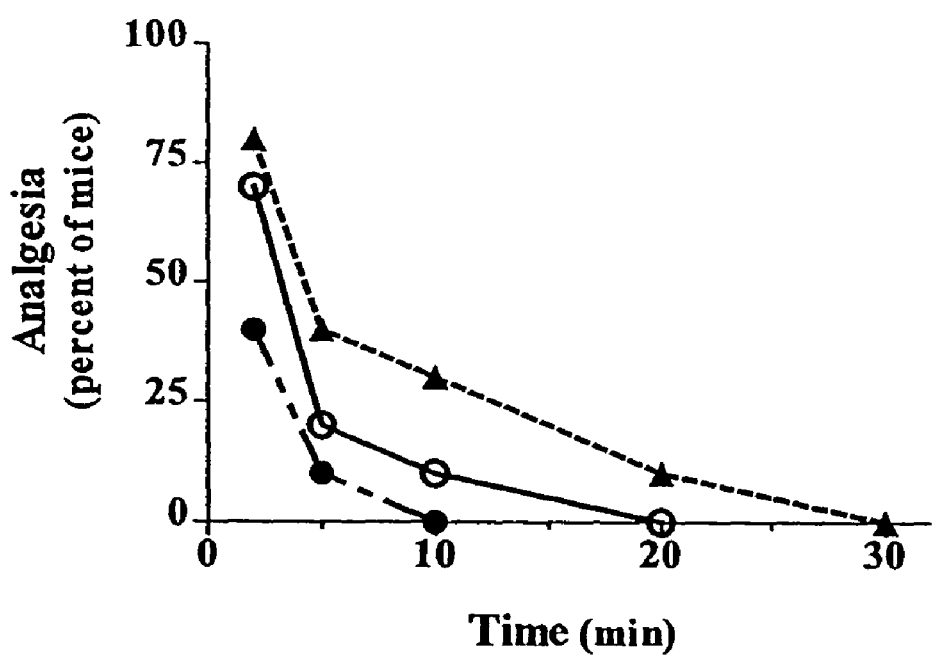

Both opioids and local anesthetics provide peripheral analgesia. Synergistic potentiation of analgesia through topical administration of a local anesthetic/opioid combination offers a new approach to peripheral pain management. Further, the ability to block tolerance with peripherally-acting NMDA antagonists is an important advancement in the clinical treatment of pain. Topical administration of a local anesthetic/opioid synergistic drug formulation, used in conjunction with an NMDA antagonist, provides a superior method for the clinical treatment of peripheral pain. It has now been found that topical administration of a composition comprising certain relative amounts of opioids and local anesthetics results in the synergistic potentiation of peripheral antinociceptive responses. Use of topically administered compositions comprising the proportions of opioids and local anesthetics described and claimed herein provides an important new approach to management of peripheral pain.

The invention encompasses a pharmaceutical composition comprising at least one opioid and at least one local anesthetic, in amounts sufficient to potentiate an antinociceptive response when the composition is administered topically in a physiologically acceptable topical excipient.

As used herein "potentiated antinociceptive response" is a pain-reducing response elicited through the synergistic effect of at least one pioid and at least one local anesthetic, in which the combined effect is greater than the sum of the effect produced by either agent alone.

The preferred opioid is morphine and, preferably, the opioid in the composition of the present invention is morphine. Other opioids are suitable, including, but not limited to, compounds based on or derived from morphine-like compounds and analogs. The opioid can be, but is not limited to, ethylmorphine, hydromorphine, morphine, oxymorphone, codeine, levorphanol, oxycodone, pentazocine, propoxyphene, fentanyl, sufentanil, lofentanil, morphine-6-glucuronide, buprenorphine, methadone, etorphine, [D-Ala$^2$,MePhe$^4$,Gly(ol)$^5$]enkephalin (DAMGO), butorphanol, nalorphine, nalbuphine, naloxone benzoylhydrazone, bremazocine, ethylketocyclazocine, U50,488, U69,593, spiradoline, naltrindole, [D-Pen$^2$,D-Pen$^5$]enkephalin (DPDPE), [D-Ala$^2$,Glu$^4$]deltorphin, and [D-Ser$^2$,Leu$^5$]enkephalin-Thr$^6$ (DSLET), [D-Ala$^2$,MePhe$^4$,Gly (ol)$^5$] enkephalin, and β-endorphin, dynorphin A, dynorphin B and α-neoendorphin and small molecule and combinatorial chemistry products thereof. As new opioids are discovered they can be effectively used in accordance with the present invention.

Lidocaine is the preferred local anesthetic in the composition of the present invention. The local anesthetic can be any known in the art, including, but not limited to, lidocaine, bupivacaine, mepivacaine, ropivacaine, tetracaine, etidocaine, chloroprocaine, prilocaine, procaine, benzocaine, dibucaine, dyclonine hydrochloride, pramoxine hydrochloride, benzocaine, and proparacaine. Most preferably, the opioid is morphine and the local anesthetic is lidocaine in the composition of the present invention.

The topical pharmaceutical composition of the invention can further comprise an NMDA receptor antagonist. These antagonists can be competitive or non-competitive drugs. The NMDA receptor antagonist can be any known in the art, including, but not limited to, dextromethorphan, dextrorphan, ketamine, pyroloquinoline quinone, cis-4-(phosphonomethyl)-2-piperdine carboxylic acid, MK801, memantine, and their mixtures and pharmaceutically acceptable salts thereof.

The invention further encompasses a method of providing topical analgesia to a subject comprising topical administration of a pharmaceutical composition comprising at least one opioid and at least one local anesthetic in a physiologically acceptable topical excipient and in an amount and a duration sufficient to potentiate an antinociceptive response.

A "subject" is a vertebrate, preferably a mammal, and more preferably a human. Mammals include but are not limited to humans, farm animals, sport animals, and pets.

The general mode of action of the composition is through "topical administration." This mode of action is restricted to the region below the surface of the skin or mucosa where the drug application has occurred. In using topical routes of administration, the amount of opioid and local anesthetic absorbed systemically is so minimal that no pharmacologic effect is produced away from the application site. Topical administration of the composition is directed to cutaneous, mucosal, vaginal, rectal, ocular, or nasal surfaces. The composition is topically administered to a subject in an amount and duration sufficient to prevent or relieve pain associated with any cause, including, but not limited to, neuropathic inflammation, and acute and chronic peripheral neuropathy.

Topical application of the composition is useful for relieving pain, inflammation and irritation associated with skin diseases and disorders, such as psoriasis, pruritus, and lesions. Painful lesions develop, for example, from viral infections, skin cancers and genetic disorders. Topical application of the composition provides relief from pain associated with wounds, insect and animal bites, abrasions and burns, including those resulting from over-exposure to the sun, chemicals, radiation or chemotherapeutic agents. Acute postoperative or surgical pain can be reduced or even prevented, as can pain associated with chronic disorders, such as arthritis.

Standard texts, such as Remington: The Science and Practice of Pharmacy, 17th edition, Mack Publishing Company, incorporated herein by reference, can be consulted to prepare suitable compositions for topical administration, without undue experimentation. Suitable dosages can also be determined based upon the text and documents cited herein.

The amount of opioid and local anesthetic necessary to produce a therapeutic effect at an affected area is based on, or related to, the size of the area and the relative condition that is to be treated. For example, the amount of opioid and local anesthetic needed to treat severe pain or inflammation is likely to be greater than the amount of opioid and local anesthetic needed to treat mild to moderate forms of the affliction. In addition, an acute condition will likely require less medication for less time than a chronic condition. Individual sensitivities will also influence the dosage amounts administered to a particular subject. A determination of the appropriate dose is within the skill of one in the art given the parameters herein. In terms of the present invention, the preferred dosage range is preferably determined by considering the amount of opioid and local anesthetic delivered, in percentage, and the surface area to be treated. The concentration of each therapeutic agent, including, for example the opioid, local anesthetic and/or NMDA receptor antagonist, in the pharmaceutical composition can be from about 0.01% to about 25%, about 0.1% to about 10%, 0.5% to about 5%, about 0.01% to about 1%, and about 0.01% to about 0.05%. In accordance with the present invention, the foregoing doses can be readily optimized following the teachings herein, based on known pharmacological protocol, by those of ordinary skill in the art, with no more than routine optimization. Of course, the preferred lower limit for drug delivery is that necessary to bring about an antinociceptive effect. The preferred upper limit is less than that amount which produces untoward side effects.

Although it is not crucial, the dilution and/or formulation of the opioid and local anesthetic in a physiologically acceptable topical excipient can be important and useful in providing the final dosage concentration. The compositions can be supplied in solid, semi-solid or liquid forms, including tablets, capsules, powders, liquids, and suspensions. The invention thus encompasses concentrated forms for subsequent dilution before use or sale. The present invention comprises any physiologically acceptable topical excipients including, but not limited to, gels, lotions, creams, ointments, and liquids.

The compositions of the present invention can be administered topically by preparing a solution of the opioid and local anesthetic in a solvent such as water, saline, aqueous dextrose, glycerol, ethanol or dimethyl sulfoxide (DMSO), with or without other excipients. The composition can also contain other medicinal agents, pharmaceutical agents, adjuvants, carriers, and auxiliary substances such as wetting, emulsifying, and pH buffering agents.

Administration to the subject is performed in accordance with that mode which is most amenable to the topically acceptable form chosen. For example, gels, lotions, creams, and ointments are preferably administered by spreading. Because hydrated skin is more permeable than dry skin, the dosage form can be modified or an occlusive dressing can be applied used to facilitate absorption. Also contemplated by this invention are slow release or sustained release forms, whereby a relatively consistent level of the opioid and local anesthetic are provided over an extended period.

A subject can be treated in accordance with the present invention by administering the opioid and the local anesthetic suspended in or admixed with a physiologically suitable topical excipient and manually applied or sprayed (either with a manually-actuated pump or with the aid of a suitable pharmaceutically-acceptable propellant) onto the surface area in need of treatment. Preferably, the composition is applied by spraying. Suitable formulations for topical application of drugs are well known to those of ordinary skill in the art and can be routinely selected.

The amount of opioid and local anesthetic to be applied varies on the choice of excipient as well. For example, when the composition is administered by spraying an alcoholic liquid solution of the drug, the total volume in a single dose can be very low. Conversely, when the opioid and local anesthetic is administered in an aqueous cream, the total volume can be higher. The excipient selected and its manner of application are preferably chosen in consideration of the needs of the patient and the preferences of the administering physician.

The following examples are provided to illustrate but not limit the claimed invention.

Example 1

The activity of topical lidocaine was assessed using a known administration paradigm. Kolesnikov and Pasternak (1999). In this procedure, the distal portion of the tail (2-3 cm) is immersed in a DMSO solution containing the indicated drugs for the stated time, typically 2 minutes.

Prior studies have documented that DMSO alone has no effect when tested in this manner in the radiant heat tailflick assay. The onset of analgesia is rapid, with peak effects seen immediately following the removal of the tail from the treatment solution. Therefore, mice were tested immediately after termination of topical administration. Testing was performed on the portion of the tail immersed in the treatment solution, since the analgesic actions of agents administered in this manner are restricted to the exposed portions of the tail, the proximal regions are not affected.

Antinociception, or analgesia, was defined quantitatively as a tailflick latency for an individual animal that was twice its baseline latency or greater. Baseline latencies typically ranged from 2.5 to 3.0 seconds, with a maximum cut-off latency of 10 seconds to minimize tissue damage in analgesic animals. Group comparisons were performed with the Fisher exact test. $ED_{50}$ values were determined with the Bliss program as previously reported. Bliss & Collingridge (1993) Nature 31; and Kolesnikov et al. (1999).

Groups of mice ($n \geq 10$) were exposed to a fixed concentration of topical lidocaine for 30 seconds, 1 minute and 2 minutes and tested by tailflick assay immediately following termination of drug exposure. Similar to morphine, the analgesic response to lidocaine was determined to be dependent upon the exposure time. FIG. 1a. Groups of mice ($n \geq 10$) were treated with lidocaine (4.3 mM or 2.15 mM) or morphine (15 mM) for 2 minutes and tested by tailflick assay over the course of 30 minutes. The response produced from a constant concentration of lidocaine increased from 20% at 30 seconds to 70% at 2 minutes. Time action curves revealed a maximal response immediately following removal of the tail from the solution, with a gradual decrease to baseline levels within 20 minutes. FIG. 1b. This response was slightly shorter in duration than a morphine dose giving the same maximal response. In comparison, a lower lidocaine dose gave both a decreased maximal response and a shorter duration of action.

Figure 2:
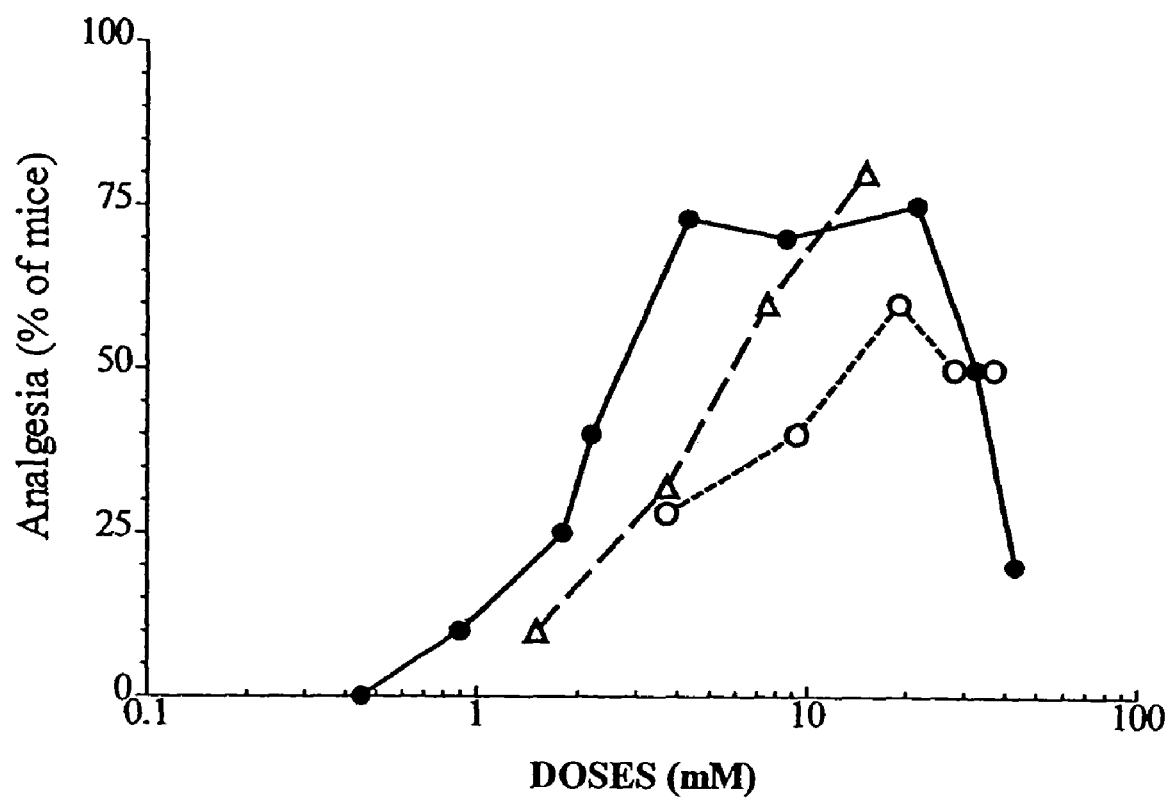
FIG. 2 is a graph depicting the effects of topical lidocaine or morphine on mice. Morphine is shown in open triangles. Lidocaine is shown in closed circles. Lidocaine HCl is shown in open circles.

Groups of mice ($n \geq 10$) were exposed to the indicated concentration of the free base of lidocaine, lidocaine HCl or morphine for 2 minutes and tested by tailflick assay immediately following termination of drug exposure. FIG. 2. Both were active, but the salt form was less effective and plateaued at a 50-60% response. As expected, the free base form of lidocaine was more active, achieving a 75% response. However, it displayed a biphasic dose-response curve with further increases in concentration beyond 20 mM, revealing a progressive lowering of analgesic activity. Morphine also was active, as previously reported, having an intermediate potency between the two forms of lidocaine. Kolesnikov and Pasternak (1999). Table 1.

TABLE 1

Analgesic potency of lidocaine and opioids alone and in combination

| Treatment | Lidocaine | | Opioid | |
| --- | --- | --- | --- | --- |
| | $ED_{50}$ Value (mM) | Ratio | $ED_{50}$ Value (mM) | Ratio |
| Lidocaine alone | 2.5 (2.0, 3.4) | | | |
| Morphine alone | | | 6.1 (4.3, 8.4) | |
| Buprenorphine alone | | | 1.1 (0.7, 1.5) | |
| Levorphanol alone | | | 5.0 (3.8, 7.8) | |
| Lidocaine/Morphine | 0.85 (0.6, 1.1) | 2.9 | 1.7 (1.2, 2.2) | 3.6 |
| Lidocaine/Levorphanol | 0.47 (0.3, 0.8) | 5.3 | 0.94 (0.6, 1.6) | 5.3 |
| Lidocaine/Buprenorphine | 0.44 (0.3, 0.6) | 5.7 | 0.18 (0.12, 0.240) | 6.1 |

Table 1 depicts $ED_{50}$ values determined from dose-response curves and presented with 95% confidence limits. For lidocaine, the $ED_{50}$ values were determined only from the initial portion of the curve. Combinations were also examined using increasing doses of a fixed ratio of the indicated drugs. $ED_{50}$ values were determined and presented with the 95% confidence limits. The relative potency of the various drugs in combination was compared to the same drug alone as a ratio. The fixed ratios of lidocaine/morphine (0.5), lidocaine/buprenorphine (2.4) and lidocaine/levorphanol (0.5) were used.

Figure 3:
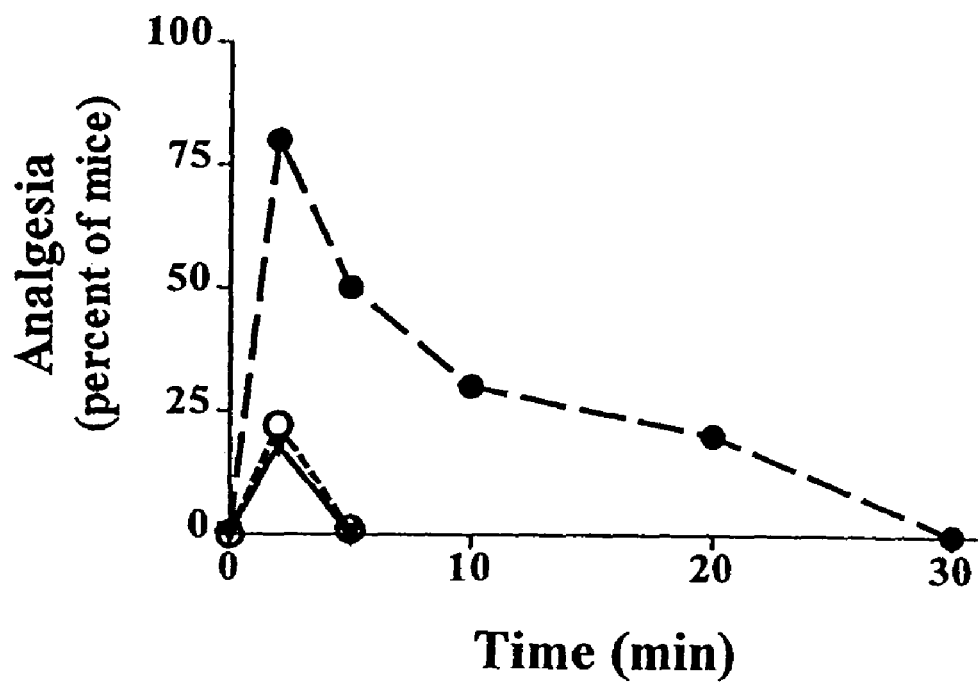
FIG. 3 is a set of graphs depicting (a) topical lidocaine and morphine interactions on groups of mice receiving either topical morphine (open circle, 1.5 mM; n=10) or lidocaine (closed triangle 0.9 mM; n=10) alone or both together (closed circle n=20).
Figure 3:
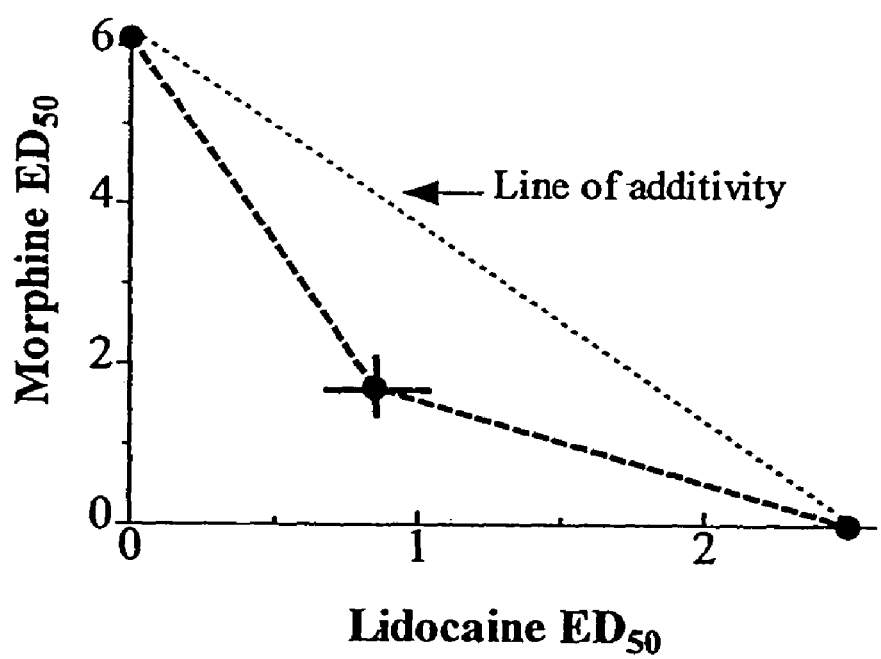

Potential interactions between lidocaine and morphine were initially assessed using a fixed, low dose of each. FIG. 3a. Alone, lidocaine and morphine produced peak responses of only 20%. Together, their peak response was 80%. This was far greater than anticipated from simple additive interactions (p<0.004). Comparing the areas under the curve gave even more dramatic differences. As anticipated, naloxone significantly reversed the effects of the combination.

Example 2

To further assess the possibility of synergy, isobolographic analysis was employed. Adams et al. (1997) J. Pharmacol. Exp. Ther. 266:1261. $ED_{50}$ values were determined for each agent alone. They were subsequently tested together at various doses and at a constant ratio based upon their respective $ED_{50}$ values. Significance was assumed by the lack of overlap of the confidence limits of the combination value with the confidence limits of the line of additivity. Only concentrations shown to be analgesic alone were used in combination with other drugs.

A dose-response curve was generated using increasing doses of a fixed ratio of lidocaine/morphine. The $ED_{50}$ value of a lidocaine/morphine combination was determined from the dose-response curve a with 95% confidence limit. FIG. 3b. Values on the axes represent the $ED_{50}$ values for the indicated drug alone and the line connecting them corresponds to simple additive interactions. FIG. 3b. Points below the line of additivity indicate synergism. The $ED_{50}$ value fell well below the line of additivity, indicating synergism. FIG. 3b. The lack of overlap of the confidence limits of the combination value with those of the line of additivity confirmed its significance. The relationship of lidocaine and morphine combinations was also explored by defining the $ED_{50}$ values of each agent alone and by analyzing a combination of fixed doses of the other agent. Table 2.

TABLE 2

Effects of fixed doses of morphine or lidocaine on the analgesic potency of various agents.

| | $ED_{50}$ (mM) | 95% Confidence limits | Shift |
|---|---|---|---|
| Lidocaine alone | 1.5 | (2.0, 3.4) | |
| + morphine 2.5 mM | 1.0 | (0.4, 1.8) | 2.5 |
| + morphine 3.0 mM | 0.8 | (0.6, 1.1) | 3.1 |
| + morphine 4.5 mM | 0.7 | (0.5, 0.9) | 3.6 |
| Morphine alone | 6.1 | (4.3, 8.4) | |
| + lidocaine 0.45 mM | 3.6 | (2.6, 4.5) | 1.7 |
| + lidocaine 0.9 mM | 1.5 | (0.9, 2.6) | 4.1 |
| + lidocaine 1.8 mM | 1.3 | (0.6, 1.3) | 4.7 |

Table 2 depicts $ED_{50}$ values with 95% confidence limits that were determined from at least three doss of topical lidocaine alone, with the indicated morphine concentration, with topical morphine alone, or with the indicated concentration of lidocaine.

Low doses of morphine with little activity alone markedly enhanced the potency of lidocaine. The effect seemed to plateau, little advantage was seen by increasing the morphine concentration from 3 to 4.5 mM. Similar results were seen with the morphine dose-response curves. Again, a low dose of lidocaine facilitated morphine analgesia, with little additional effect seen after doubling the lidocaine concentration from 0.9 to 1.8 mM. Thus, the enhanced activity of the drug combinations was most evident at low concentrations of each.

Figure 4:
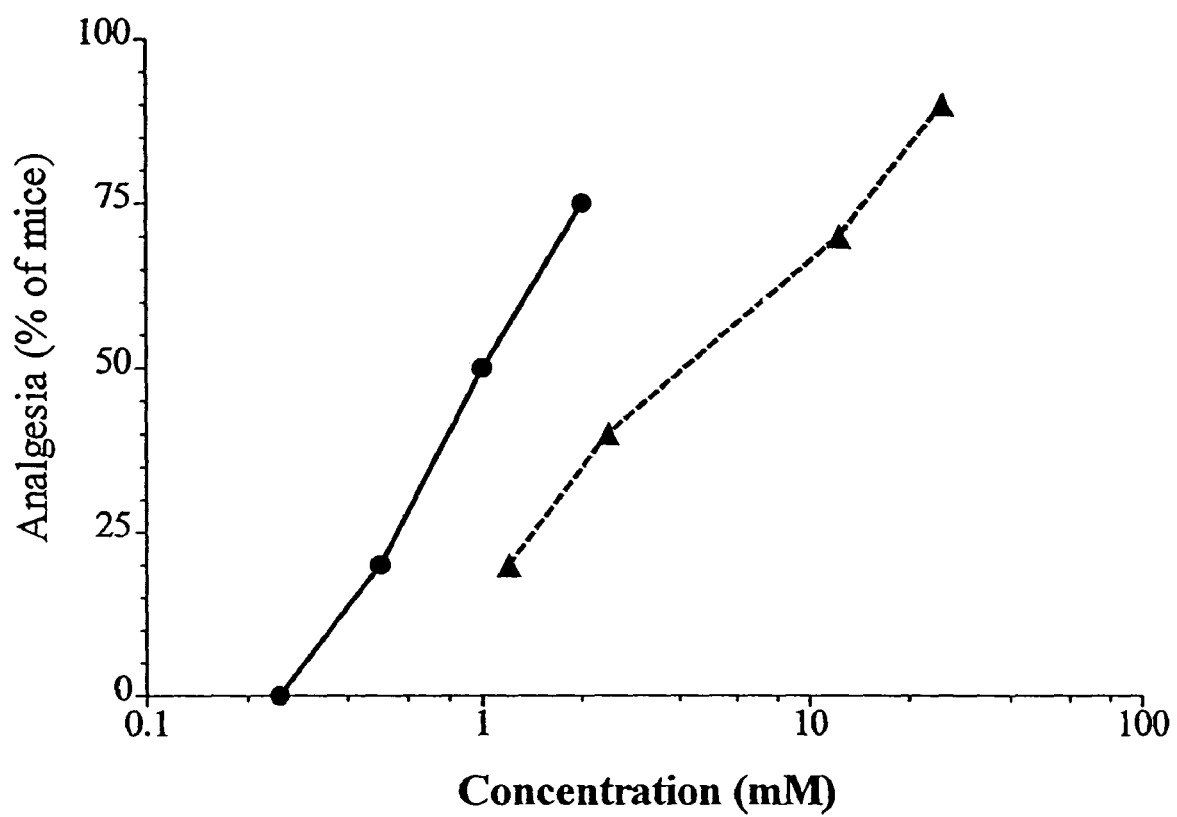
FIG. 4 is a graph depicting the effects of topical buprenorphine (closed circle) and levorphanol (closed triangle) in mice.

Whether the synergy seen with morphine/lidocaine combinations extends to opioids which function through alternative classes of opioid receptors, including levorphanol and buprenorphine, was tested. Groups of nice (n≧10) were exposed to increasing concentrations of the drugs for 2 minutes and tested by tailflick assay immediately following termination of drug exposure. Topically, levorvanol and buprenorphine both yielded full analgesic responses, with $ED_{50}$ values of 5.0 and 1.1 mM, respectively. FIG. 4, Table 1.

Figure 5:
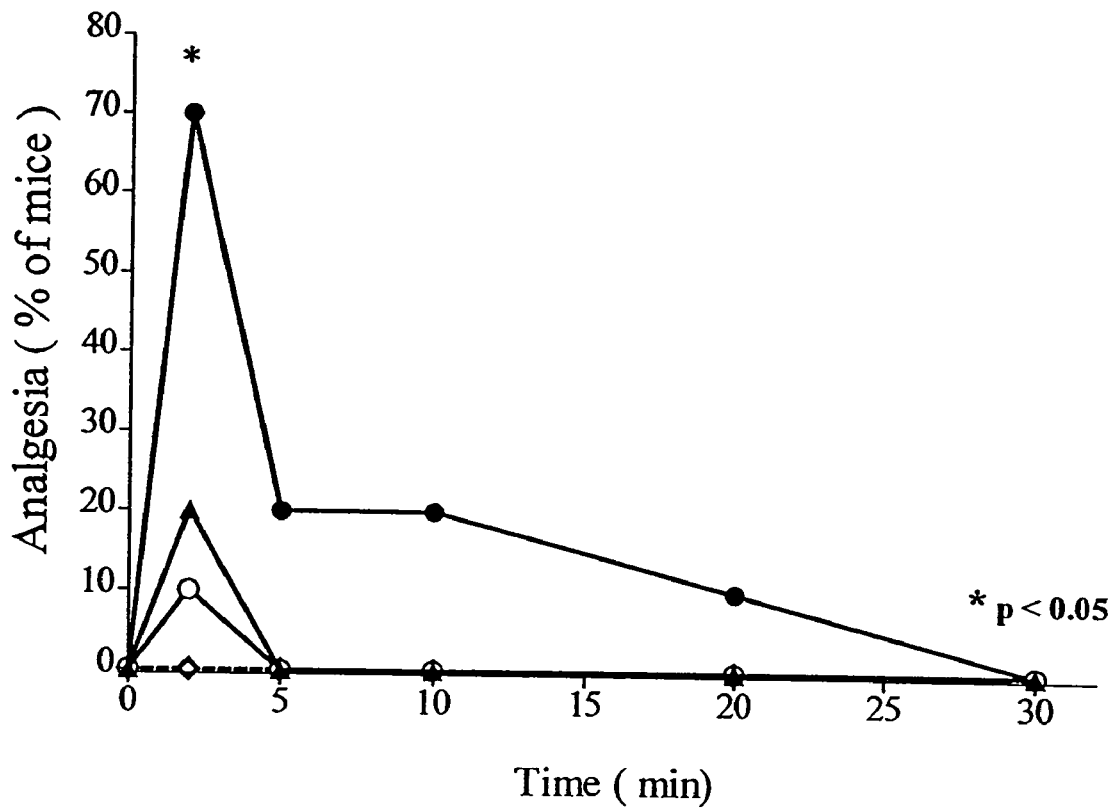
FIG. 5 is a set of graphs depicting the effects of combinations of low doses of opioids with and without lidocaine in mice. In 5a, lidocaine alone is shown by a closed triangle; levorphanol alone is shown by an open circle, a mixture of lidocaine, levorphanol and naloxone is shown by an open diamond.
Figure 5:
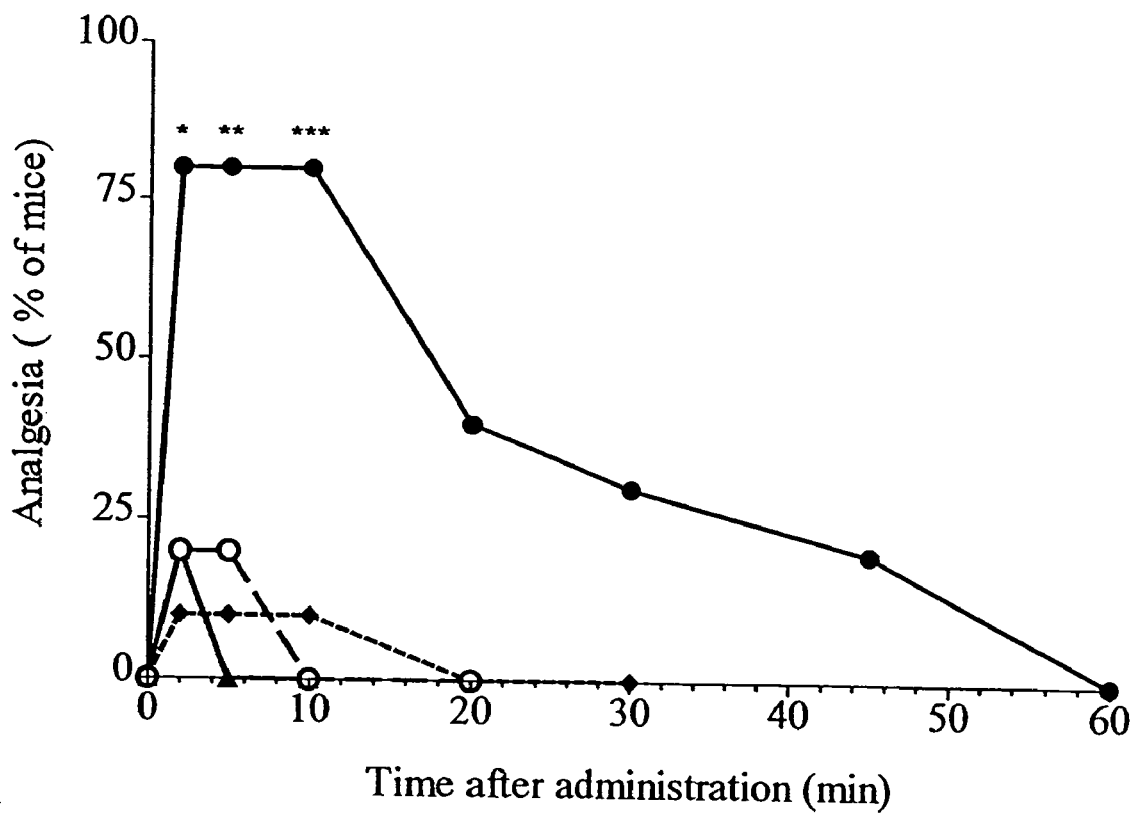

Combinations of low doses of lidocaine with these opioids also produced greater than additive analgesic action. Groups of mice (n=20) received either topical lidocaine (0.9 mM) or levorphanol (1.8 mM) or the combination thereof for 2 minutes and were tested by tailflick assay over the course of 30 minutes. A second group of mice received naloxone (1 mg/kg, s.c.) 20 minutes before the topical drug application. FIG. 5a. The results obtained with levorphanol closely resembled those obtained with morphine. Specifically, the combination of low lidocaine and levorphanol doses gave a maximal response, far beyond that expected by simple additive interactions (p<0.03) as well as a prolonged duration far exceeding that of either drug alone. FIG. 5a. Each drug alone had no effect beyond 5 minutes. In comparison, when used together, the response lasted for more than 20 minutes. The effects of the combination of doses were readily antagonized by naloxone.

Buprenorphine and lidocaine gave similar results. Groups of mice (n=20) received either topical lidocaine (0.9 mM) or buprenorphine (0.5 mM) or the combination thereof for 2 minutes and were tested by the tailflick assay over the course of 60 minutes. Another group of mice received naloxone (1 mg/kg, s.c.) 20 minutes before the topical drug application. FIG. 5b. The maximal responses of the two together were far beyond those anticipated by simple additive interactions. FIG. 5b. The duration of the response for the combination was also markedly different from that of either agent alone. Alone, each drug lasted less than 10 minutes. In contrast, the duration of the response of the combination was quite prolonged. The peak effect of the combination was 80% and persisted for 10 minutes. Analgesia could still be demonstrated after 45 minutes. The duration of the response from the lidocaine/buprenorphine combination exceeded that seen with any of the other opioids tested. Naloxone significantly lowered the response of the combination.

Figure 6:
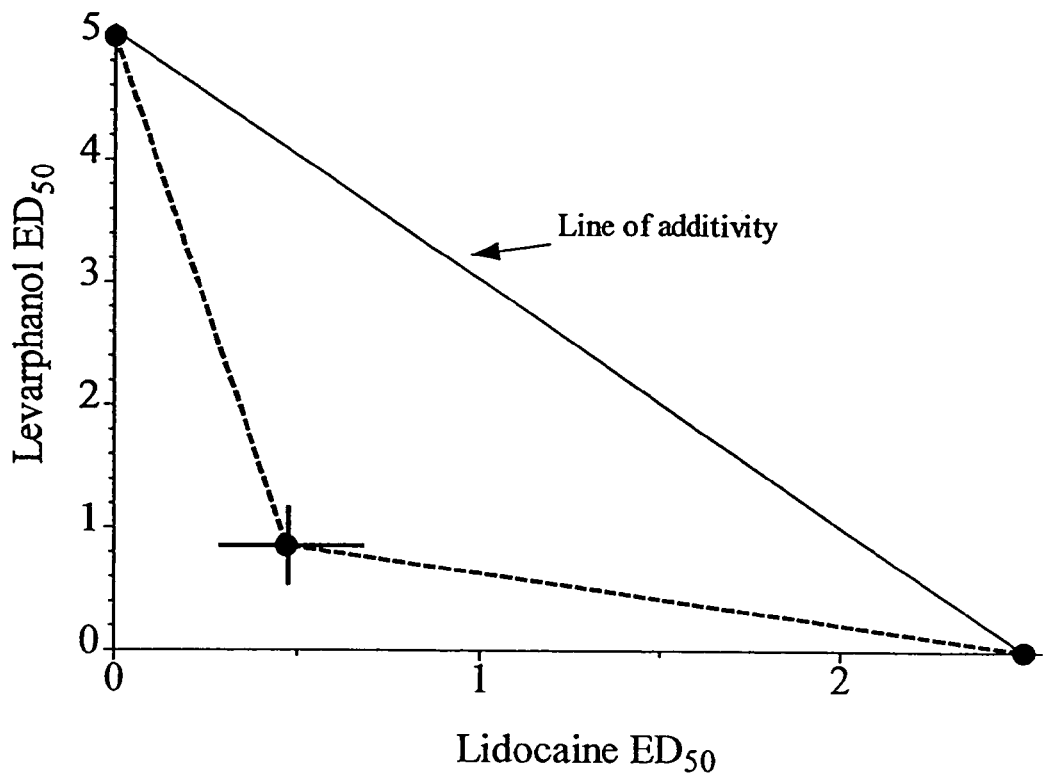
FIG. 6 depicts isobolographic analysis of lidocaine interactions with levorphanol (a) and buprenorphine (b) in mice.
Figure 6:
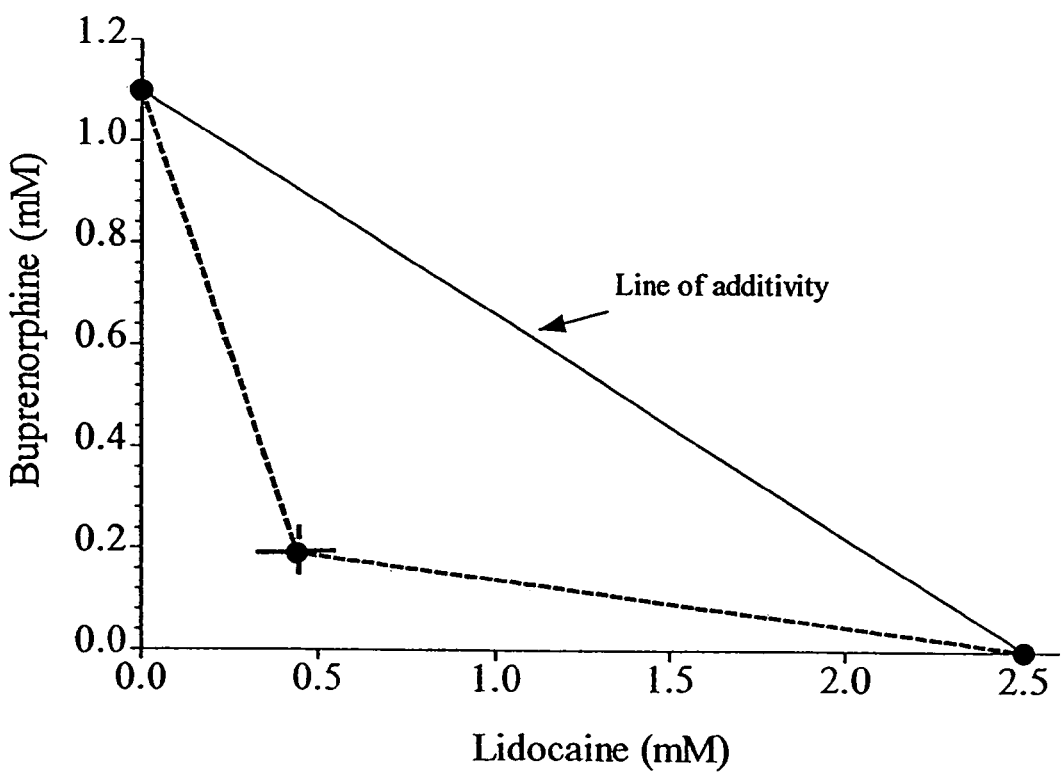

Combinations of the additional opioids were next examined by isobolographic analysis, using dose-response curves with fixed ratios of the two drugs in combination. FIG. 6 and Table 1. Combining levorphanol with lidocaine enhanced their relative potencies over 5-fold, more than the enhancement of morphine by lidocaine, consistent with synergy. FIG. 6a. A fixed lidocaine/buprenorphine ratio of 0.17 was used to determine the $ED_{50}$ value of the combination with 95% confidence limits from the dose-response curve. The point falls below the line of additivity between the $ED_{50}$ values for each drug alone, indicating synergy. A fixed lidocaine/buprenorphine ratio of 0.4 was used to determine the $ED_{50}$ value of the combination with 95% confidence limits from the dose-response curve. FIG. 6b. Again, the point falls below the line of additivity between the $ED_{50}$ values for each drug alone, indicating synergy. In combination, buprenorphine and lidocaine, shifted their individual $ED_{50}$ values approximately 6-fold. FIG. 6b.

Example 3

To test the potential utility of the combination of morphine and Lidocaine, a subject received topical administration of either Lidocaine alone (0.125 mg/ml), morphine alone (0.25 mg/ml) or both together at the same respective concentrations. All dosages were in a gel formulation comprised of 50% carboxymethylcellulose and 50% DMSO. The subject was blinded as to the identity of the gels. The gels were applied on the subject's finger for 20 minutes, after which the finger was placed under a radiant light heat source and the latency to the point of severe discomfort determined and compared to a baseline latency obtained prior to the application of the gel.

Figure 7:
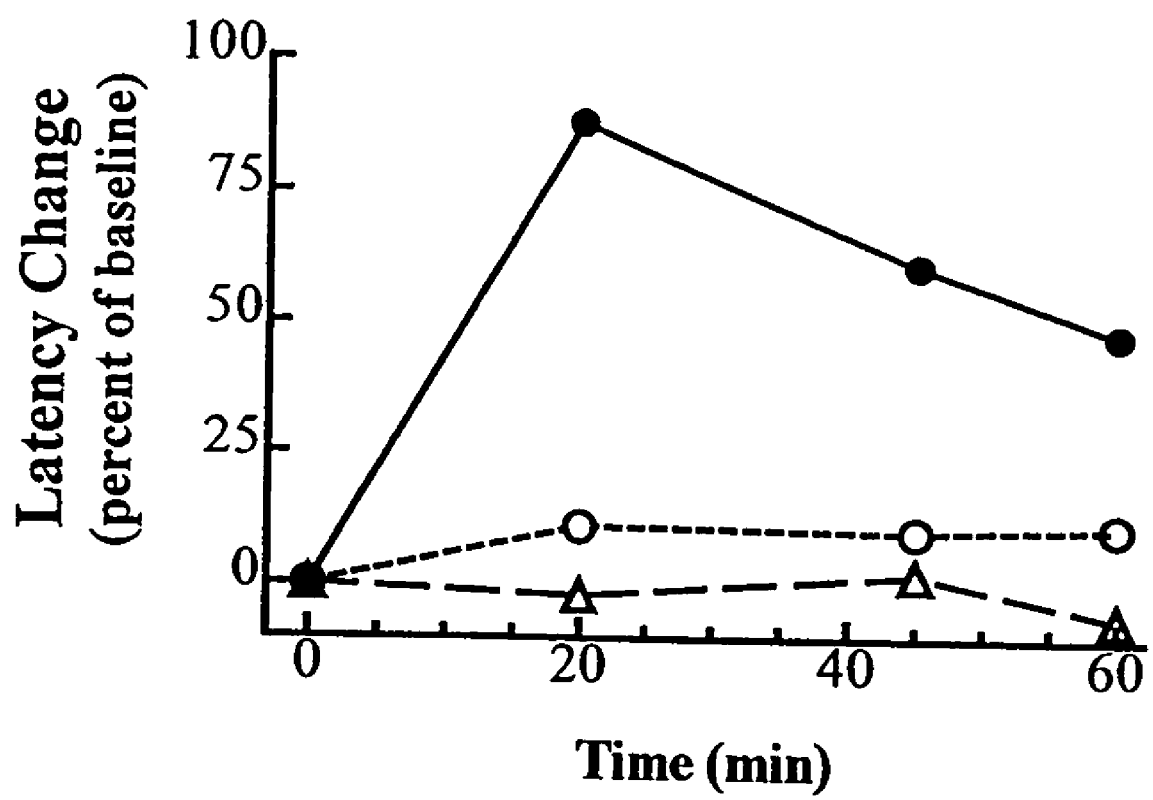
FIG. 7 is a graph depicting differences in latency change between morphine alone (open circles); Lidocaine alone (open triangles); and morphine and Lidocaine (closed circles).

The results are presented as a percent change compared to the respective baseline latency (combination, 3.8 sec; morphine alone 4.6 sec; Lidocaine alone, 5.1 sec). FIG. 7. Neither morphine nor Lidocaine produced appreciable changes in latency compared to baseline values. In contrast, the latency of the combination gel increased over 85% at 20 minutes and gradually declined over the next 40 minutes. These results confirm that the combination is synergistic compared to either morphine or Lidocaine alone.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

The invention claimed is:

1. A method of providing topical analgesia to a subject comprising topically administering to peripheral sites in the subject a pharmaceutical composition comprising (i) synergistically effective amounts of morphine and butamben and (ii) a physiologically acceptable topical excipient, to potentiate analgesia at the peripheral sites, wherein morphine and butamben are present in a ratio of about 1:0.4.

2. The method according to claim 1, wherein the pharmaceutical composition contains morphine in a dose of about 0.1% to about 10% of the composition.

3. The method according to claim 1, wherein the pharmaceutical composition contains morphine in a dose of about 0.5% to about 5% of the composition.

4. The method according to claim 1, wherein the pharmaceutical composition contains butamben in a dose of about 0.5% to about 5% of the composition.

5. The method according to claim 1, wherein the pharmaceutical composition contains butamben in a dose of about 0.01% to about 1% of the composition.

6. The method according to claim 1, wherein the pharmaceutical composition contains butamben in a dose of about 0.01% to about 0.05% of the composition.

7. The method according to claim 1, wherein the pharmaceutical composition further comprises a tolerance attenuating or preventing NMDA receptor antagonist and wherein the NMDA receptor antagonist is selected from the group consisting of dextromethorphan, dextrorphan, ketamine, pyroloquinoline quinone, cis-4-(phosphonomethyl)-2-piperdine carboxylic acid, MK801, memantine, and their mixtures and pharmaceutically acceptable salts thereof.

8. The method according to claim 7, wherein the pharmaceutical composition contains the NMDA receptor antagonist in a dose of about 0.01% to about 25% of the composition.

9. The method according to claim 7, wherein the pharmaceutical composition contains the NMDA receptor antagonist in a dose of about 0.1% to about 15% of the composition.

10. The method according to claim 7, wherein the pharmaceutical composition contains the NMDA receptor antagonist in a dose of about 0.5% to about 5% of the composition.

11. The method according to claim 7, wherein the pharmaceutical composition contains the NMDA receptor antagonist in a dose of about 0.01% to about 1% of the composition.

12. The method according to claim 7, wherein the pharmaceutical composition contains the NMDA receptor antagonist in a dose of about 0.01% to about 0.05% of the composition.

13. The method according to claim 1, wherein topical administration of the pharmaceutical composition is provided to cutaneous, mucosal, vaginal, rectal, ocular, or nasal surfaces.

14. The method according to claim 1, wherein the pharmaceutical composition is topically administered to a subject in an amount and duration sufficient to prevent or relieve acute and chronic peripheral neuropathy.

* * * * *

UNITED STATES PATENT AND TRADEMARK OFFICE
CERTIFICATE OF CORRECTION

PATENT NO. : 7,820,688 B2
APPLICATION NO. : 10/823365
DATED : October 26, 2010
INVENTOR(S) : Gavril Pasternak Page 1 of 1

It is certified that error appears in the above-identified patent and that said Letters Patent is hereby corrected as shown below:

Specification

In column 1, beginning at line 22 and ending at line 25 please delete:

"This work was supported by the government, in part, by grants from The National Institute of Drug Abuse, No. DA 07241. The government may have certain rights to this invention."

and insert:

--This invention was made with government support under grant number DA000405 awarded by National Institutes of Health. The government has certain rights in the invention.--

Signed and Sealed this
Seventeenth Day of May, 2016

Michelle K. Lee
*Director of the United States Patent and Trademark Office*